United States Patent
Ding et al.

(10) Patent No.: US 11,224,478 B2
(45) Date of Patent: Jan. 18, 2022

(54) ELECTROSURGICAL INSTRUMENTS FOR CONTROLLING THERMAL DAMAGE

(71) Applicant: COVIDIEN LP, Mansfield, MA (US)

(72) Inventors: Weijiang Ding, Shanghai (CN); Jianjiang Chen, Shanghai (CN); Daniel A. Joseph, Golden, CO (US); Kai Liu, Hunan (CN); William H. Nau, Jr., Longmont, CO (US); Arlen K. Ward, Englewood, CO (US); William Ross Whitney, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 933 days.

(21) Appl. No.: 15/742,717

(22) PCT Filed: Jul. 17, 2015

(86) PCT No.: PCT/CN2015/084306
§ 371 (c)(1),
(2) Date: Jan. 8, 2018

(87) PCT Pub. No.: WO2017/011935
PCT Pub. Date: Jan. 26, 2017

(65) Prior Publication Data
US 2018/0199986 A1    Jul. 19, 2018

(51) Int. Cl.
*A61B 18/14* (2006.01)
*A61B 18/00* (2006.01)

(52) U.S. Cl.
CPC ...... *A61B 18/1445* (2013.01); *A61B 18/1442* (2013.01); *A61B 2018/0063* (2013.01);
(Continued)

(58) Field of Classification Search
CPC ............ A61B 18/1445; A61B 18/1442; A61B 2018/00077; A61B 2018/00083;
(Continued)

(56) References Cited

U.S. PATENT DOCUMENTS 5,026,370 A   6/1991 Lottick
5,599,350 A   2/1997 Schulze et al.
(Continued)

FOREIGN PATENT DOCUMENTS

EP   2243439 A1   10/2010

OTHER PUBLICATIONS

Supplementary European Search Report issued in corresponding European Application No. EP 15898491.4 dated Feb. 28, 2019, 6 pages.

*Primary Examiner* — Jaymi E Della
(74) *Attorney, Agent, or Firm* — Carter, DeLuca & Farrell LLP (57) ABSTRACT

An end effector assembly (114) includes a first jaw member (114a) having a first tissue contact surface (122) and a second jaw member (114b) having a second tissue contact surface (122). The second jaw member (114b) is pivotally coupled to the first jaw member (114a). The tissue contact surfaces (122) may include raised steps (122b) that define an exhaust channel (124). A longitudinally extending knife slot (214) may be defined in one or both of the tissue contact surfaces (122). One or more exhaust slots (216), which may be defined in one or both of the tissue contact surfaces (122), are in communication with the knife slot (214). The exhaust channel (124) and the exhaust slots (216) direct fluid away from the jaw members (114a, 114b) to minimize thermal damage risks associated with tissue sealing.

18 Claims, 8 Drawing Sheets

(52) U.S. Cl.
CPC ............... *A61B 2018/00077* (2013.01); *A61B 2018/00083* (2013.01); *A61B 2018/1455* (2013.01); *A61B 2218/007* (2013.01)

(58) Field of Classification Search
CPC .... A61B 2018/0063; A61B 2018/1455; A61B 2218/007
See application file for complete search history.

(56) References Cited

U.S. PATENT DOCUMENTS

| | | | |
|---|---|---|---|
| 5,797,958 A * | 8/1998 | Yoon ................... | A61B 17/122 606/139 |
| 6,273,887 B1 * | 8/2001 | Yamauchi .......... | A61B 18/1442 606/48 |
| 6,887,240 B1 * | 5/2005 | Lands ................... | A61B 17/29 606/207 |
| 8,444,664 B2 | 5/2013 | Balanev et al. | |
| 8,623,003 B2 | 1/2014 | Lau et al. | |
| 8,636,687 B1 | 1/2014 | Latterell | |
| 2003/0114851 A1 * | 6/2003 | Truckai .............. | A61B 18/1445 606/51 |
| 2003/0125728 A1 | 7/2003 | Nezhat et al. | |
| 2009/0270852 A1 * | 10/2009 | Takashino .......... | A61B 18/1445 606/27 |
| 2011/0319886 A1 * | 12/2011 | Chojin ............... | A61B 18/1445 606/37 |
| 2013/0255063 A1 | 10/2013 | Hart et al. | |
| 2013/0267947 A1 | 10/2013 | Orszulak | |
| 2014/0214019 A1 | 7/2014 | Baxter, III et al. | |
| 2015/0080879 A1 * | 3/2015 | Trees ................. | A61B 18/1445 606/40 |
| 2015/0148804 A1 | 5/2015 | Rooks et al. | |

* cited by examiner

ELECTROSURGICAL INSTRUMENTS FOR CONTROLLING THERMAL DAMAGE

TECHNICAL FIELD

The present disclosure relates to electrosurgery, and more particularly to surgical devices, systems, and methods for controlling electrosurgical thermal damage during a tissue sealing process.

BACKGROUND

Energy-based medical devices such as electrosurgical instruments are typically used in conjunction with energy sources (external energy sources or portable energy sources incorporated into the instruments themselves) to apply and control the application of energy to tissue to thermally treat, e.g., heat, tissue to achieve a desired tissue effect. Electrosurgical forceps, for example, utilize both the mechanical clamping action of the jaw members and the energy provided by the energy source and delivered to tissue to heat tissue grasped between the jaw members to achieve a desired tissue effect, e.g., to seal tissue.

One challenge associated with the sealing process is avoiding unnecessary tissue damage, particularly nerve damage, resulting from thermal spread that may occur during the tissue sealing process.

SUMMARY

Accordingly, the present disclosure is directed to new electrosurgical instruments, systems, and methods that provide efficient and effective tissue sealing by limiting risks associated with thermal spread during tissue sealing. The presently disclosed electrosurgical instruments and/or systems include end effectors with jaw members defining exhaust slots and/or exhaust channels. Advantageously, these exhaust slots and/or exhaust channels direct fluid (e.g., steam) away from the jaw members of the end effector to enable effective and efficient tissue sealing while limiting undesirable thermal spread.

In one aspect, the present disclosure relates to an end effector assembly having a first jaw member including a first tissue contact surface and a second jaw member including a second tissue contact surface. The second jaw member is pivotally coupled to the first jaw member. One or both of the first and second tissue contact surfaces may be configured to electrically couple to an electrosurgical energy source to receive electrosurgical energy from the electrosurgical energy source. A longitudinally extending knife slot is defined in one or both of the first and second tissue contact surfaces.

An exhaust slot is defined in one or both of the first and second tissue contact surfaces. The exhaust slot extends transverse to the longitudinally extending knife slot and is in communication with the longitudinally extending knife slot. The exhaust slot is configured to direct fluid toward the longitudinally extending knife slot and away from the first and second jaw members. In some embodiments, the exhaust slot is angled relative to the knife slot. The exhaust slot may extend between an open end in communication with the longitudinally extending knife slot to a closed end. In some embodiments, the closed end is distal to the open end. The exhaust slot may be curved between the open and closed ends.

In some embodiments, the first and second jaw members have a tip-biased configuration.

According to another aspect, the present disclosure is directed to a method for controlling fluid during a tissue sealing process. The method involves grasping tissue between a pair of jaw members pivotally coupled together, activating energy to seal tissue grasped between the pair of jaw members, capturing fluid within one or more exhaust slots defined within a tissue contact surface of one of the pair of jaw members as tissue is sealed between the pair of jaw members, and directing the fluid from one or more exhaust slots to a longitudinally extending knife slot of one or both of the pair of jaw members and away from the pair of jaw members.

Directing the fluid from the one or more exhaust slots may include directing the fluid through one or more exhaust slots at an angle relative to the longitudinally extending knife slot and across one or both of the pair of jaw members. The method may involve directing the fluid proximally through the longitudinally extending knife slot.

In yet another aspect, an end effector assembly includes a first jaw member and a second jaw member pivotally coupled to the first jaw member between an open position and a closed position. In the closed position, the first and second jaw members may be movable between an unpinched position and a pinched position. The first and second jaw members may be tip-biased.

A central longitudinal axis extends distally along the first and second jaw members. A first tissue contact surface has a first raised step that extends longitudinally along the first jaw member. A second tissue contact surface has a second raised step that extends longitudinally along the second jaw member. The first and second raised steps are disposed in complementary relation relative to the central longitudinal axis.

An exhaust channel is defined between the first and second raised steps when the first and second jaw members are in the closed position. The exhaust channel is configured to direct fluid away from the first and second jaw members. The exhaust channel may be configured to direct fluid proximally along the first and second jaw members. The first and second tissue contact surfaces may have L-shaped cross-sectional profiles that complement one another to form the exhaust channel. In some embodiments, a proximal end of the exhaust channel is open and a distal end of the exhaust channel is closed. The first and second jaw members may define a closed tip distal to the exhaust channel that blocks the exhaust channel when the first and second jaw members are in the closed position. In some embodiments, the closed tip includes an insulated coating.

In some embodiments, each of the first and second jaw members includes a grasp portion and a beam portion extending from the grasp portion. The grasp portion of the first jaw member supports the first tissue contact surface and the grasp portion of the second jaw member supports the second tissue contact surface. The beam portions of the first and second jaw members define a space therebetween when the first and second jaw members are in the closed position. The exhaust channel may be configured to direct fluid generated during a tissue sealing process through the exhaust channel and proximally toward the space defined between the beam portions to limit thermal spread formed alongside the first and second jaw members during the tissue sealing process.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Particular embodiments of the present disclosure are described hereinbelow with reference to the accompanying drawings in which like reference numerals designate identical or corresponding elements in each of the several views. As used herein, the term "distal" refers to that portion of the system, device, and/or component(s) thereof, which is farther from the user, while the term "proximal" refers to that portion of the system, device, and/or component(s) thereof, which is closer to the user. In the following description, well-known functions or constructions are not described in detail to avoid obscuring the present disclosure in unnecessary detail.

Surgical systems in accordance with the present disclosure can include endoscopic and/or open surgical instruments such as forceps devices, ultrasonic dissection devices, and/or any other suitable surgical devices. Obviously, different electrical and mechanical connections and considerations apply to each particular type of device; however, the aspects and features of the present disclosure remain generally consistent regardless of the particular device used. For a detailed discussion of the construction and operation of example surgical devices, reference may be made to U.S. Patent Application Publication No. 2013/0255063 and/or U.S. Pat. No. 8,444,664, the entirety of each of which is incorporated herein by reference.

In the interest of brevity, surgical systems of the present disclosure will only be described herein in connection with an open electrosurgical forceps.

Figure 1:
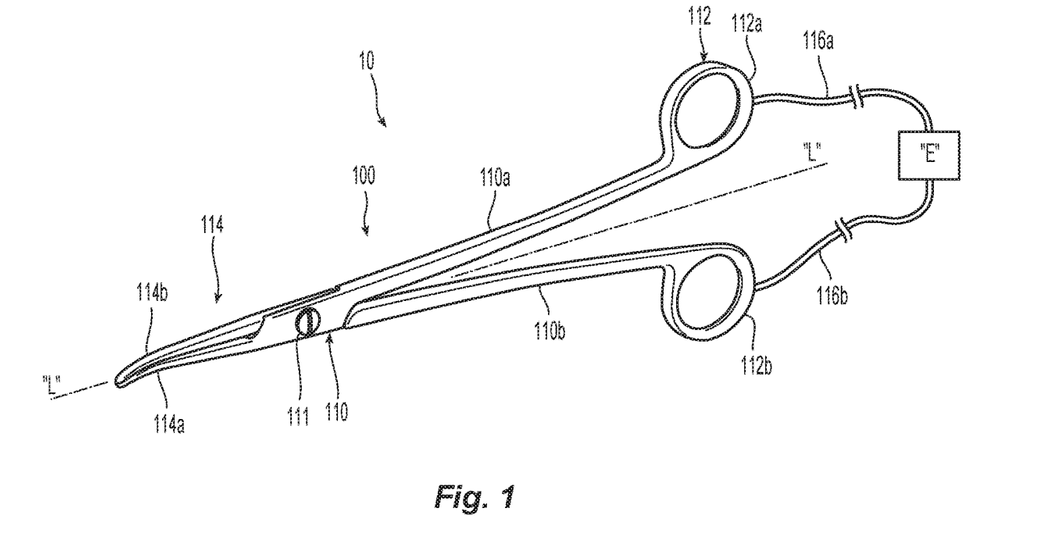
FIG. 1 is a perspective view of an electrosurgical instrument illustrated in a closed position in accordance with the principles of the present disclosure.

Turning now to FIG. 1, an electrosurgical system, in accordance with the present disclosure, generally referred to as 10, includes an open electrosurgical forceps 100 that electrically couples to an electrosurgical energy source "E."

Electrosurgical forceps 100 and/or electrosurgical energy source "E" can be configured to perform monopolar and/or bipolar electrosurgical procedures, including, for example, cutting, coagulation, ablation, and vessel sealing procedures. Electrosurgical energy source "E" may include a plurality of outputs for interfacing with various electrosurgical instruments such as electrosurgical forceps 100 and/or any other suitable energy modality. Electrosurgical energy source "E" may be powered by direct (e.g., DC or a battery) and/or by alternating current. Electrosurgical energy source "E" may include one or more converting devices for converting from DC to AC or vice a versa.

Electrosurgical forceps 100 includes a body 110 including a first arm 110a and a second arm 110b that are pivotally coupled together by a pin 111. Embodiments of electrosurgical forceps 100 can include configurations of Allis clamps, Babcock clamps, hemostats, tweezers, forceps, and other suitable graspers.

First and second arms 110a, 110b support a handle portion 112 including a pair of handles 112a, 112b at a proximal end of first and second arms 110a, 110b and an end effector 114 having a pair of jaw members 114a, 114b at a distal end of first and second arms 110a, 110b. Handle portion 112 is operable to selectively move/pivot the pair of jaw members 114a, 114b between open and closed positions for grasping and/or sealing tissue (not shown) therebetween as described in greater detail below. At least a portion of body 110 can include electrically conductive material (e.g., metallic material or the like) that can be an electrically conductive surface. In some embodiments, only portions of body 110 include electrically conductive materials and/or surfaces, such as, for example, one or both of the pair of jaw members 114a, 114b. In certain embodiments, the entire body 110 is electrically conductive. Body 110, or portions thereof, can include insulation material which may be provided as a layer or coating.

One or more supply and/or return lines 116a, 116b extend proximally from body 110 and are disposed in electrical communication with the electrically conductive material/surface(s) of body 110. The one or more supply and return lines 116a, 116b are configured to couple the electrically conductive material/surfaces of body 110 to electrosurgical energy source "E" (e.g., via one or more terminals (not shown) of electrosurgical energy source "E") for electrically communicating with electrosurgical energy source "E."

For a detailed discussion of the construction and operation of example of similar electrosurgical devices and/or electrosurgical energy sources, reference may be made to U.S. Patent Application Publication No. 2013/0267947 and/or U.S. Pat. No. 5,026,370, each of which is incorporated herein by reference.

Figure 2:
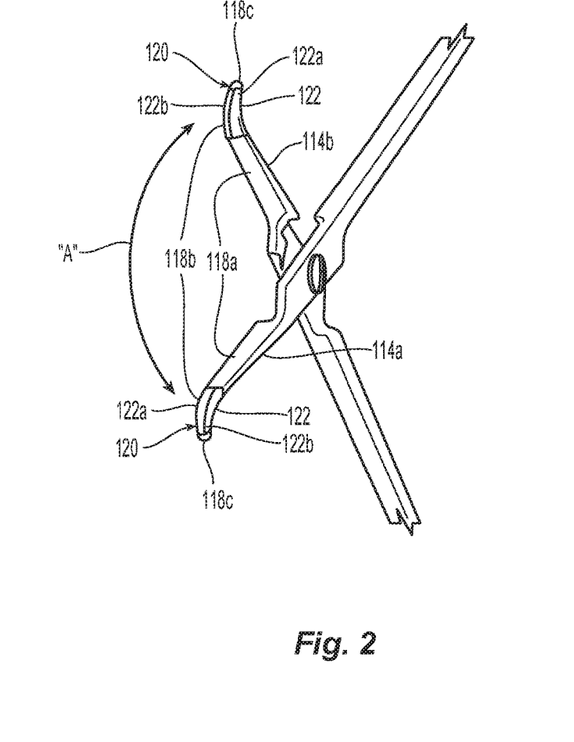
FIG. 2 is a perspective view of a distal portion of the electrosurgical instrument of FIG. 1 in an open position.

Referring to FIGS. 1 and 2, first and second jaw members 114a, 114b are movable relative to one another between a closed position (FIG. 1) and an open position (FIG. 2), as indicated arrow "A." Each of first and second jaw members 114a, 114b includes a beam portion 118a and a grasp portion 118b that extends distally from beam portion 118a to a distal tip 118c. Distal tips 118c support insulation material that may be coated thereon.

Figure 3A:
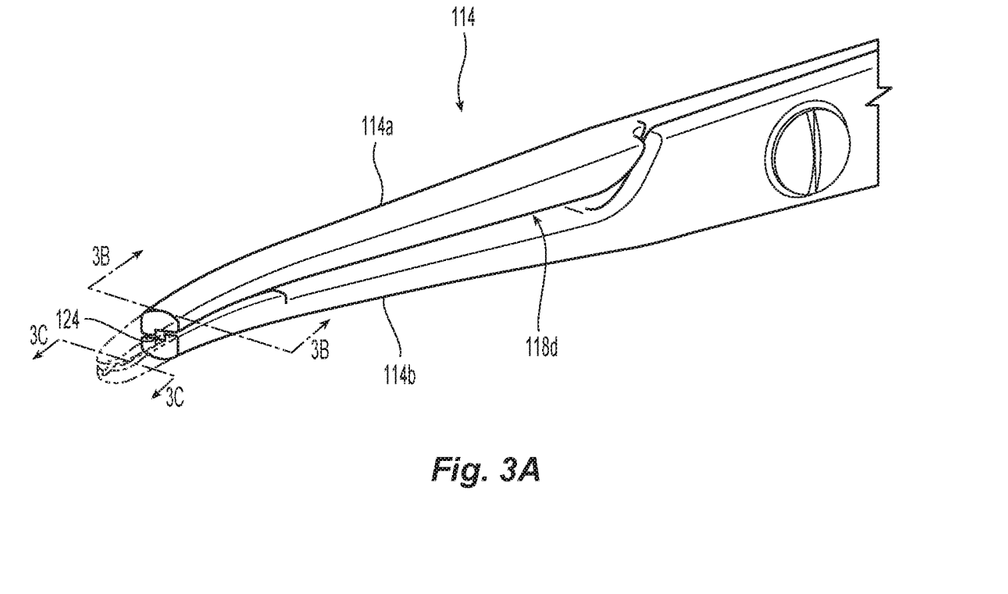
FIG. 3A is an enlarged, perspective view of a distal portion of the end effector of FIG. 3A with a distal tip thereof shown in phantom for clarity.
Figure 3B:
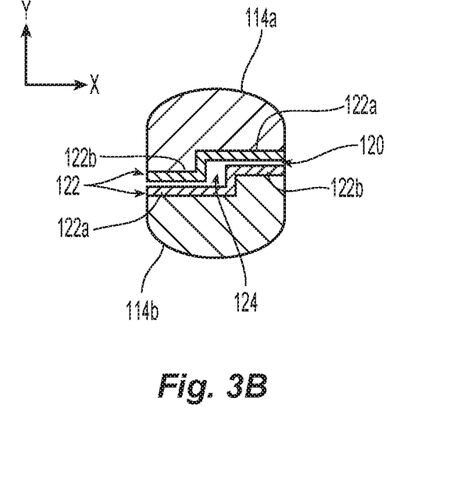
FIG. 3B is an enlarged, cross-sectional view of the end effector of FIG. 3A as taken along section line 3B-3B.
Figure 3C:
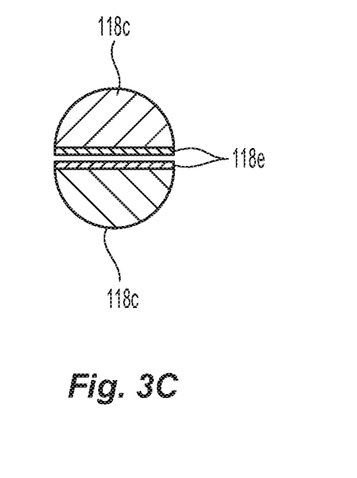
FIG. 3C is an enlarged, cross-sectional view of the end effector of FIG. 3A as taken along section line 3C-3C.

With reference to FIGS. 3A and 3B, grasp portion 118b supports a sealing plate 120 having a stepped tissue contact surface 122 that extends longitudinally along longitudinal axis "L-L" (FIG. 1). As seen in FIG. 3B, each stepped tissue contact surface 122 includes a base step 122a and a raised step 122b that is vertically and horizontally offset from base step 122a such that base and raised steps 122a, 122b have different heights in the y-direction (e.g., vertical) and different widths in the x-direction (e.g., horizontal). Base step 122a is wider than raised step 122b such that stepped tissue contact surfaces 122 of first and second jaw members 114a, 114b are complementary (e.g., reciprocal counterparts of one another) and define an exhaust channel 124 between stepped tissue contact surfaces 122 when first and second jaw members 114a, 114b are in the closed position. Exhaust channel 124 may be centrally disposed and/or coaxially aligned with longitudinal axis "L-L" of end effector 114.

Figure 4A:
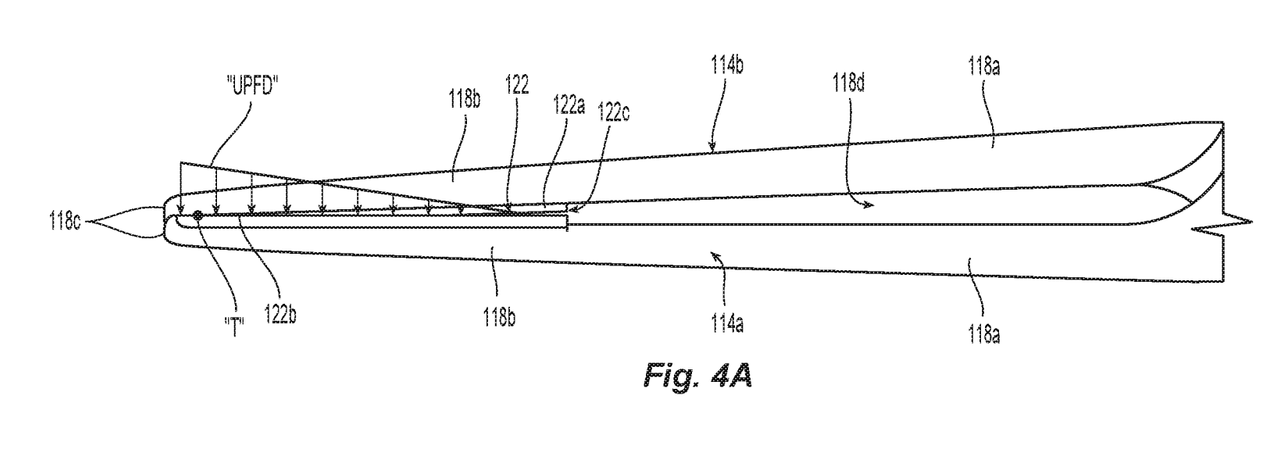
FIG. 4A is an enlarged, side view of a distal portion of an end effector of the electrosurgical instrument of FIG. 1, the electrosurgical instrument shown in the closed position with the end effector in an unpinched condition.
Figure 4B:
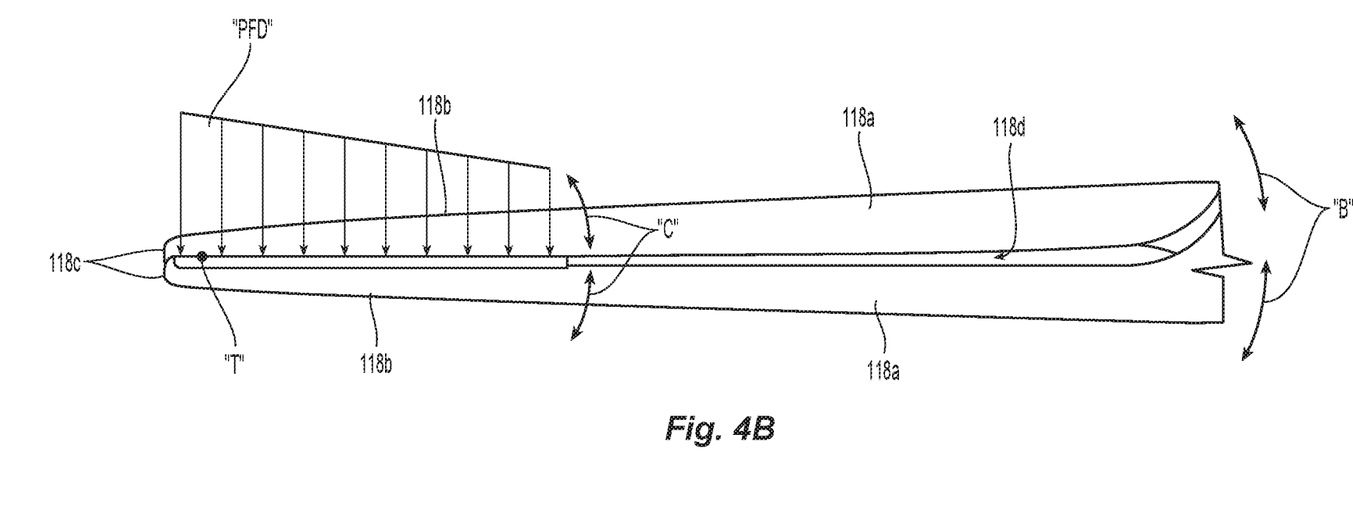
FIG. 4B is an enlarged, side view of the distal portion of the end effector of FIG. 3A with the end effector shown in a pinched condition.
Figure 5:
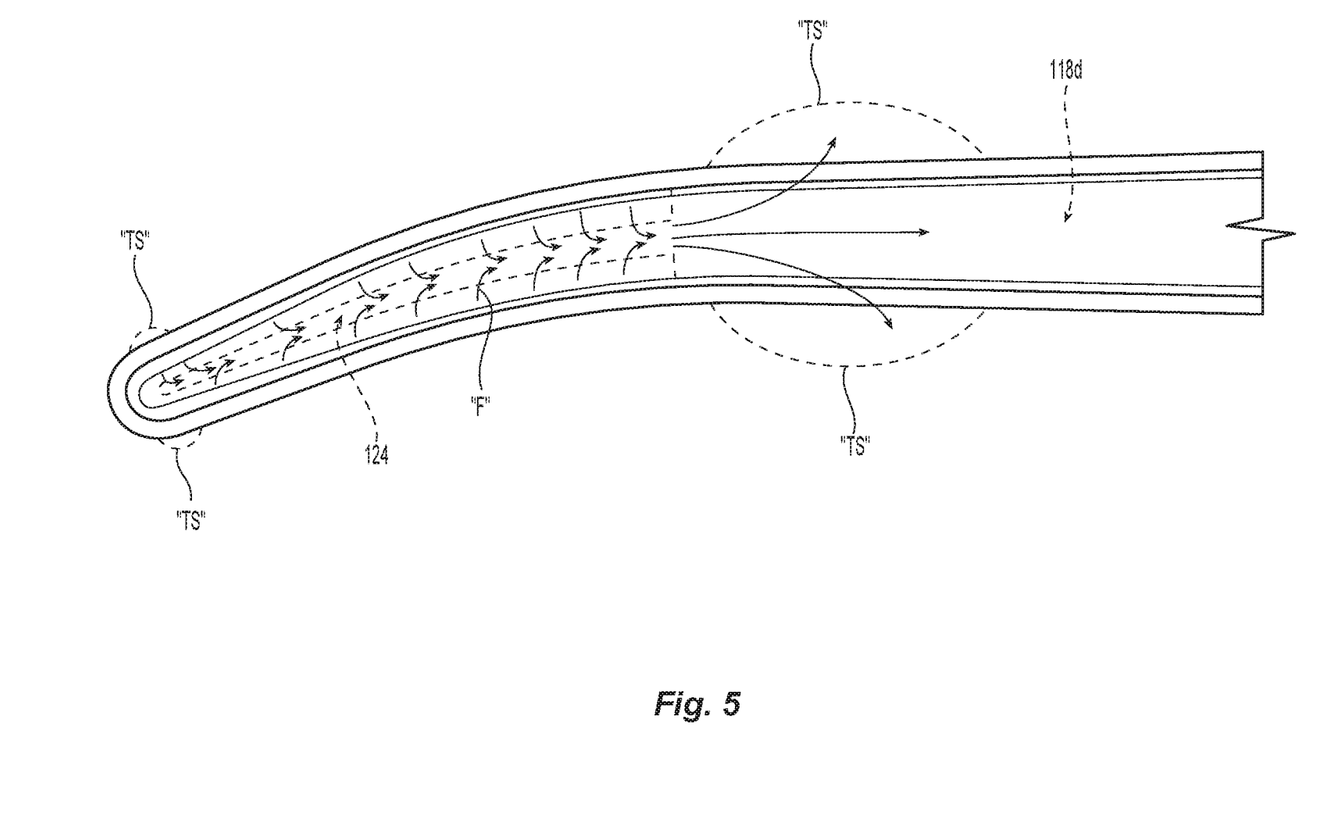
FIG. 5 a schematic, top view of the end effector of FIG. 4A illustrating direction of flow through an exhaust channel of the end effector of FIG. 4A.

Referring to FIGS. 4A, 4B, and 5, exhaust channel 124 extends proximally from distal tips 118c of first and second jaw members 114a, 114b to a space 118d defined between beam portions 118a of first and second jaw members 114a, 114b while first and second jaw members 114a, 114b are in the closed position. Exhaust channel 124 functions to direct flow of fluid "F" (e.g., steam) generated during a tissue sealing process of tissue "T" proximally through exhaust channel 124 toward space 118d to reduce heating of fluid "F" on tissue contact surfaces 122 and limit thermal spread "TS" adjacent first and second jaw members 114a, 114b, as described in greater detail below.

Stepped tissue contact surfaces 122 of grasp portions 118b of first and second jaw members 114a, 114b are positioned to engage one another in unpinched (FIG. 4A) and pinched positions (FIG. 4B) while first and second jaw members 114a, 114b are in the closed position. As indicated by arrows "B" and "C," beam portions 118a of first and second jaw members 114a, 114b are movable relative to one another to move grasp portions 118b of first and second jaw members 114a, 114b between the unpinched and pinched positions. For instance, first and second jaw members 114a, 114b are movable between the unpinched and pinched positions to effectuate tissue sealing of tissue "T" grasped between grasp portions 118b of first and second jaw members 114a, 114b as described in greater detail below.

Grasp portions 118b of first and second jaw members 114a, 114b are tip-biased such that distal portions grasp portions 118b contact one another before proximal portions of grasp portions 118b contact one another as first and second jaw members 114a, 114b move from the unpinched position to the pinched position.

With reference to FIG. 4A, in the unpinched position, distal portions 122b of stepped tissue contact surfaces 122 of first and second jaw members 114a, 114b are in contact while proximal portions 122a of stepped tissue contact surfaces 122 define an angled space or gap 122c between stepped tissue contact surfaces 122 of first and second jaw members 114a, 114b. In this unpinched position, one or more contact forces (e.g., pressure) may be exerted between the first and second jaw members 114a, 114b, as illustrated by arrows of unpinched force distribution "UPFD."

In the pinched position, seen in FIG. 4B, proximal and distal portions 122a, 122b of stepped tissue contact surfaces 122 of first and second jaw members 114a, 114b are in contact and exert gripping, squeezing and/or sealing forces (e.g., pressure) between grasp portions 118b of first and second jaw members 114a, 114b, as illustrated by arrows of pinched force distribution "PFD." The contact and/or gripping/squeezing/sealing forces of unpinched force distribution "UFPD" and/or pinched force distribution "PFD" may change and/or be uniform along at least portions of grasp portions 118b of first and second jaw members 114a, 114b. For example, pressure at a proximal end of stepped tissue contact surfaces 122 (e.g., adjacent angle space 122c) may be lower than pressure at a distal end of stepped tissue contact surfaces 122 (e.g., adjacent distal tips 118c). As another example, sealing pressure along grasp portions 118b of first and second jaw members 114a, 114b may be uniform and/or increase toward distal tips 118c. Sealing pressure exerted along at least portions of grasp portions 118b while first and second jaw members 114a, 114b are in the pinched position may be greater than contact pressure exerted along at least portions of grasp portions 118b while first and second jaw members 114a, 114b are in the unpinched position.

In use, once desired pressure is applied to tissue "T" grasped between first and second jaw members 114a, 114b in the pinched position, as illustrated in FIG. 4B, electrosurgical energy source "E," is activated to electrically communicate with sealing plate 120 and enable stepped tissue contact surfaces 122 to seal the grasped tissue "T." During the sealing process, fluid "F," such as steam, is released from the grasped tissue "T." With distal tips 118c of first and second jaw members 114a, 114b providing a block or distal barrier to exhaust channel 124, effectively closing a distal end of exhaust channel 124, proximal displacement/exhaustion of fluid "F" may be facilitated as a function of the pinched force distribution "PFD." For example, with greater force/pressure adjacent distal ends of grasp portions 118b of first and second jaw members 114a, 114b, as compared to proximal ends of grasp portions 118b, fluid "F" is urged into exhaust channel 124 and displaced, directed and/or exhausted in a proximal direction.

As seen in FIG. 5, exhaust channel 124 directs fluid "F" proximally through exhaust channel 124 and into space 118d. As fluid "F" passes through exhaust channel 124 and into space 118d, a temperature of fluid "F" may decrease as a function of time, distance, and/or heat transfer into ambient air. Advantageously, as a result of decreases in temperature of fluid "F," redirection of fluid "F," and/or displacement of fluid "F" provided by the features of exhaust channel 124 and/or space 118d of first and second jaw members 114a, 114b, risks of undesirable thermal spread "TS" associated with first and second jaw members 114a, 114b is significantly reduced.

Figure 6:
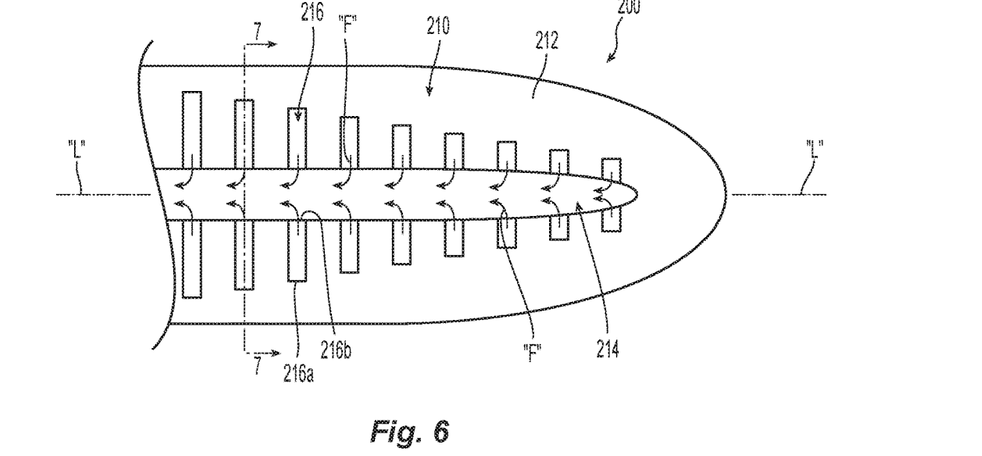
FIG. 6 is a top view of a portion of a jaw member of another embodiment of an end effector according to the principles of the present disclosure.
Figure 7:
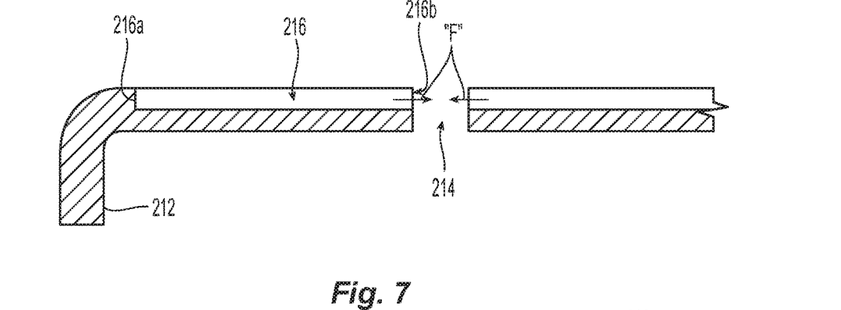
FIG. 7 is a partial, enlarged, cross-sectional view of a seal plate of the jaw member of FIG. 6 as taken along section line 7-7.

Turning now to FIGS. 6 and 7, another embodiment of an end effector includes a first jaw member 200 having a seal plate 210. A second jaw member (not shown), which opposes first jaw member 200, may include an identical or substantially identical seal plate 210. Seal plate 210 includes a tissue contact surface 212 defining a longitudinally extending knife slot 214 that extends along longitudinal axis "L-L" of this embodiment of the end effector. Longitudinally extending knife slot 214 receives a knife (not shown) therein to severe tissue grasped between the jaw members. Transverse exhaust slots 216, which may be orthogonal to knife slot 214, are defined within seal plate 210 on one or both opposed sides of knife slot 214. Exhaust slots 216 extend across seal plate 210 and include a closed end 216a and an open end 216b. Open end 216b is in communication with knife slot 214. Adjacent exhaust slots 216 may be longitudinally and/or laterally offset from one another.

In use, exhaust slots 216 capture fluid "F" generated during a tissue sealing process and direct the captured fluid "F" into knife slot 214. Knife slot 214 receives fluid "F" and directs and/or exhausts the captured fluid "F" proximally through knife slot 214.

Figure 8:
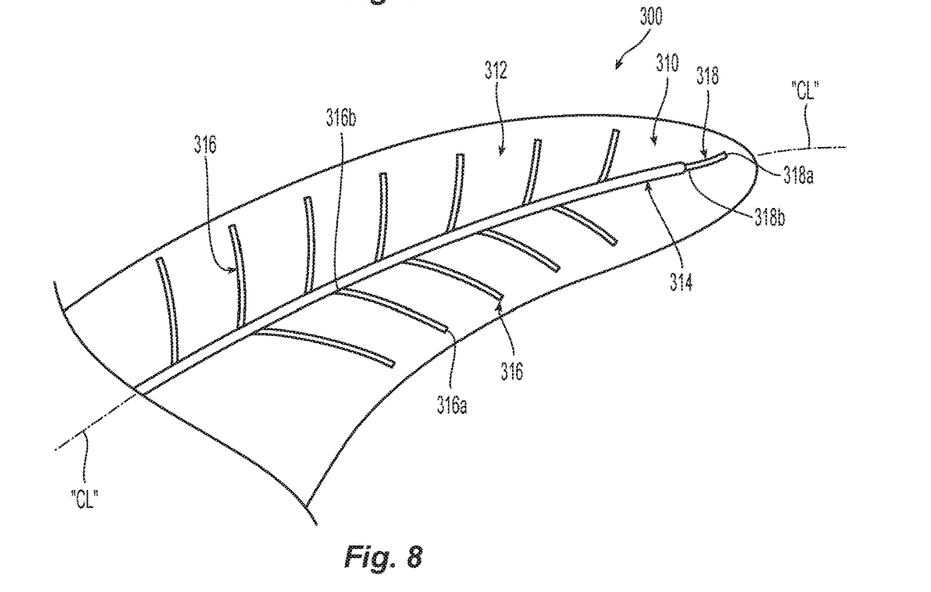
FIG. 8 is top view of a portion of another jaw member of still another embodiment of an end effector according to the principles of the present disclosure.

With reference to FIG. 8, another embodiment of an end effector includes first jaw member 300 having a seal plate 310. First jaw member 300 and seal plate 310 are substantially similar to first jaw member 200 and seal plate 210. A second jaw member (not shown), which opposes first jaw member 300, may include an identical or substantially identical seal plate 310.

Seal plate 310 includes a tissue contact surface 312 defining a longitudinally extending knife slot 314 that extends along a centerline "CL-CL" of the end effector. Transverse exhaust slots 316 are defined within seal plate 310 on one or both opposed sides of knife slot 314. Transverse exhaust slots 316 extend across seal plate 310 and include a closed end 316a and an open end 316b. Open end 316b is in communication with knife slot 314. Open end 316b is disposed proximal to closed end 316a. In some embodiments, open end 316b is disposed distal to closed end 316a. One or more exhaust slots 316 may extend transversely to knife slot 314 such that exhaust slot 316 is non-parallel to, and non-orthogonal to, knife slot 314. One or more co-linear exhaust slots 318 extend longitudinally along seal plate 310 and are co-linear with knife slot 314 and/or centerline "CL-CL" of the end effector. Co-linear exhaust slot 318 includes an open end 318a that is proximal to closed end 318b. Exhaust slots 316, 318 may be longitudinally and/or laterally offset from one another. One or more of jaw member 300, seal plate 310, knife slot 314, transverse exhaust slots 316, and co-linear exhaust slots 318 may be at least partially curved.

Figure 9A:
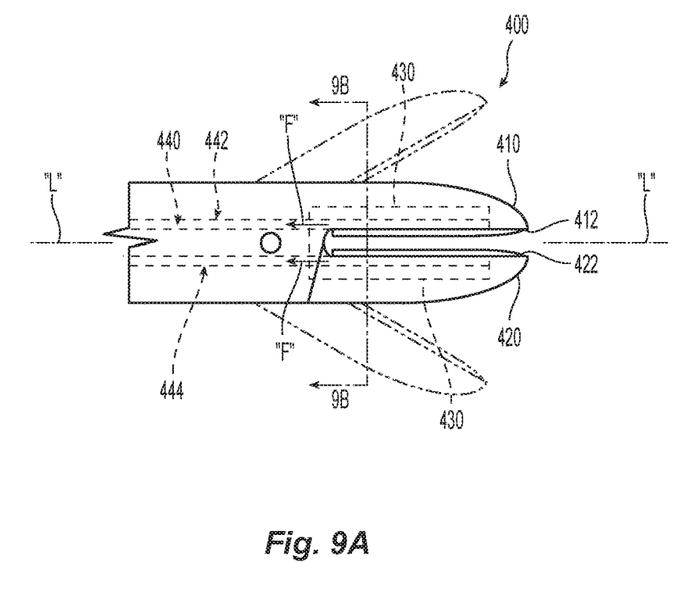
FIG. 9A is a side view of another embodiment of an end effector according to the principles of the present disclosure.
Figure 9B:
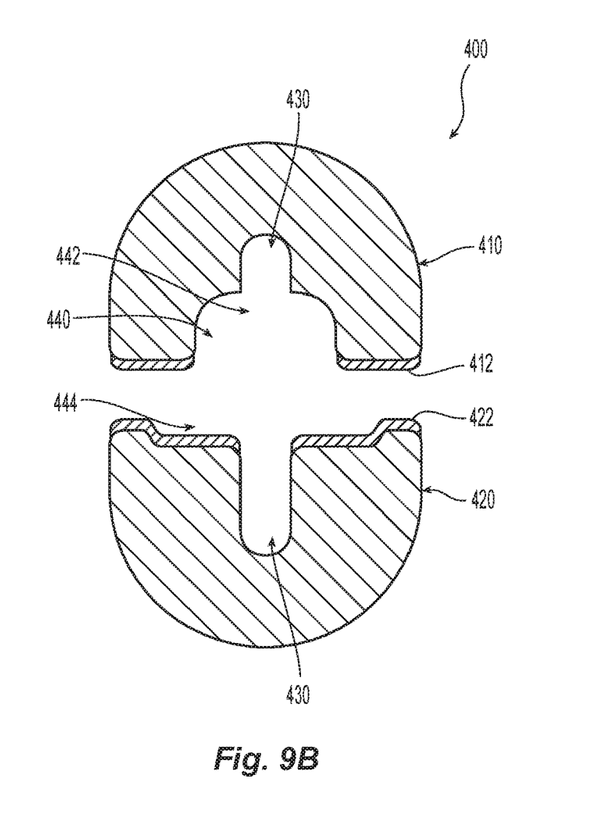
FIG. 9B is an enlarged, cross-sectional view of the end effector of FIG. 9A as taken along section line 9B-9B.

Turning now to FIGS. 9A and 9B, yet another embodiment of an end effector 400 includes a first jaw member 410 and a second jaw member 420. First jaw member 410 includes a first seal plate 412 and second jaw member 420 includes a second seal plate 422. A longitudinally extending knife slot 430 is defined by first and second jaw members 410, 420. An exhaust channel 440 in communication with knife slot 430 extends longitudinally along longitudinal axis "L-L" on opposed sides of knife slot 430. Exhaust channel 440 functions to proximally exhaust fluid "F" alone and/or in conjunction with knife slot 430 during a tissue sealing process similar to other embodiments described herein. Exhaust channel 440 includes a first jaw channel 442 defined with first jaw member 410 and second jaw channel 444 defined within second jaw member 420. In some embodiments, exhaust channel 440, first and second jaw channels 442, 444, and/or portions thereof, extend only along one side of knife slot 430. In certain embodiments, exhaust channel 440 includes only one of first and second jaw channels 442, 444. In some embodiments, exhaust channel 440, first and second jaw channels 442, 444, and/or portions thereof, extend above and/or below knife slot 430 along longitudinal axis "L-L."

Figure 10:
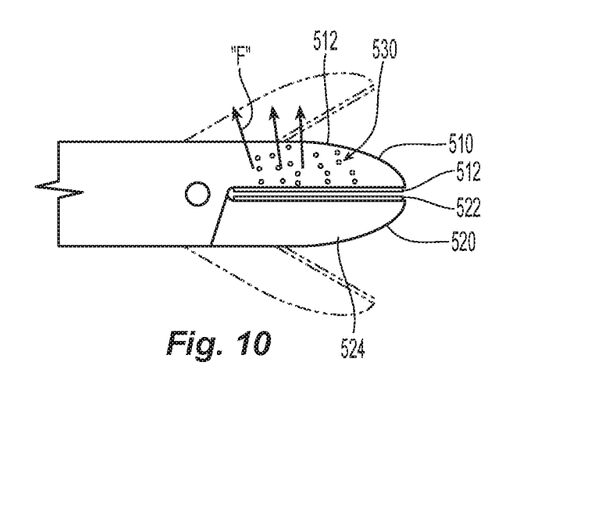
FIG. 10 is a side view of one embodiment of an end effector according to the principles of the present disclosure.

As seen in FIG. 10, one embodiment of an end effector 500 includes first and second jaw members 510, 520 including first and second seal plates 512, 522. First and/or second jaw members 510, 520 define one or more holes 530 therethrough that receive and/or direct fluid "F" from between first and second jaw members 510, 520 and out through outer surfaces 514, 524 of one or both of first and second jaw members 510, 520 during a tissue sealing process. Holes 530 may be in communication with a knife slot (not shown) of first and/or second jaw members 510, 520.

Figure 11A:
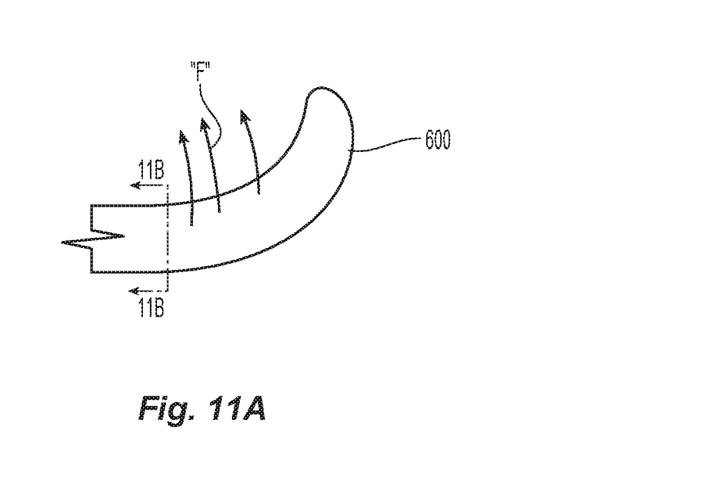
FIG. 11A is a side view of another embodiment of an end effector according to the principles of the present disclosure.
Figure 11B:
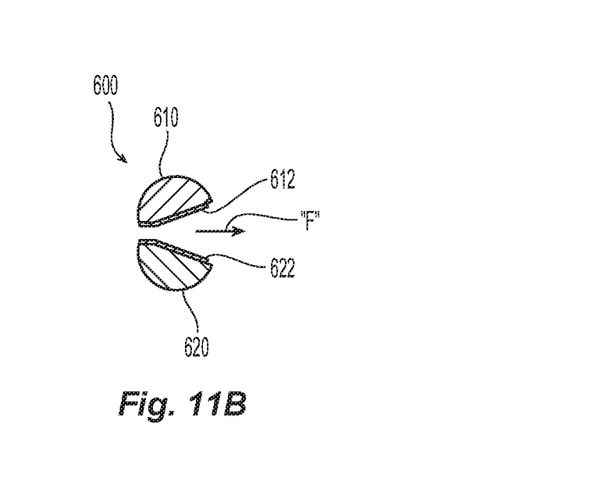
FIG. 11B is a cross-sectional view of the end effector of FIG. 11A as taken along section line 11B-11B.

Turning now to FIGS. 11A and 11B, another embodiment of an end effector 600 includes first and second jaw members 610, 620 having first and second seal plates 612, 622. One or both of at least portions of first and second jaw members 610, 620 and/or first and second seal plates 612, 622 are angled laterally outwardly away from a centerline "CL-CL" thereof and/or from the opposing jaw member and/or seal plate 610, 612, 620, 622 to direct fluid "F" from/out of one side of first and second jaw members 610, 620 during a tissue sealing process.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 12:
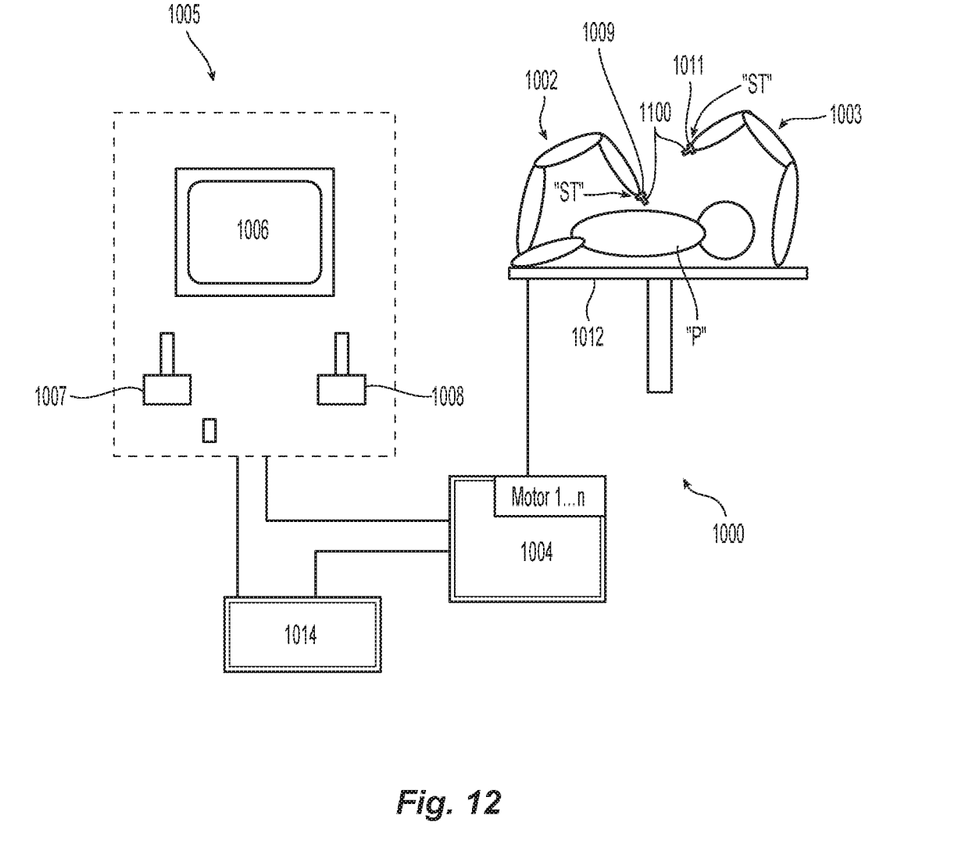
FIG. 12 is a schematic illustration of a medical work station and operating console in accordance with the present disclosure.

Referring also to FIG. 12, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient "P" lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being "P" and/or anatomical atlases.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An end effector assembly comprising:
a first jaw member;
a second jaw member pivotally coupled to the first jaw member and movable along a vertical plane between an open position and a closed position relative to the first jaw member;
a central longitudinal axis that extends distally along the first and second jaw members;
a first tissue contact surface having a first raised step extending longitudinally along the first jaw member, the first step consisting of two horizontal walls interconnected by a single vertical wall, wherein the single vertical wall is parallel to the central longitudinal axis;
a second tissue contact surface having a second raised step extending longitudinally along the second jaw member, the first raised step and the second raised step disposed in complementary relation relative to the central longitudinal axis; and
an exhaust channel defined between the first raised step and the second raised step when the second jaw member is in the closed position, the exhaust channel configured to direct fluid away from the first and second jaw members.

2. The end effector of claim 1, wherein the first and second tissue contact surfaces have L-shaped cross-sectional profiles that complement one another to form the exhaust channel.

3. The end effector of claim 1, wherein the first and second jaw members define a closed tip distal to the exhaust channel that blocks the exhaust channel when the first and second jaw members are in the closed position.

4. The end effector of claim 3, wherein the closed tip includes an insulated coating.

5. The end effector of claim 1, wherein the first and second jaw members are tip-biased.

6. The end effector of claim 1, wherein a proximal end of the exhaust channel is open and a distal end of the exhaust channel is closed.

7. The end effector of claim 1, wherein in the closed position, the first and second jaw members are movable between an unpinched position and a pinched position.

8. The end effector of claim 1, wherein each of the first and second jaw members includes a grasp portion and a beam portion extending from the grasp portion, the grasp portion of the first jaw member supporting the first tissue contact surface, the grasp portion of the second jaw member supporting the second tissue contact surface, the beam portions of the first and second jaw members defining a space therebetween when the first and second jaw members are in the closed position.

9. The end effector of claim 8, wherein the exhaust channel is configured to direct fluid generated during a tissue sealing process through the exhaust channel and proximally toward the space defined between the beam portions to limit thermal spread formed alongside the first and second jaw members during the tissue sealing process.

10. The end effector of claim 1, wherein the exhaust channel is configured to direct fluid proximally along the first and second jaw members.

11. The end effector of claim 1, wherein the single vertical wall of the first raised step is parallel to the vertical plane.

12. The end effector of claim 11, wherein the single vertical wall of the first raised step is offset from the central longitudinal axis.

13. The end effector of claim 1, wherein the second raised step consists of two horizontal walls interconnected by a vertical wall.

14. The end effector of claim 13, wherein the single vertical wall of the first raised step is parallel to the vertical plane, and wherein the vertical wall of the second raised step is parallel to the vertical plane.

15. The end effector of claim 14, wherein the single vertical wall of the first raised step is offset from the central longitudinal axis, and wherein the vertical wall of the second raised step is offset from the central longitudinal axis.

16. The end effector of claim 1, wherein the tissue contact surface of the second jaw member includes a single vertical wall that is parallel to the central longitudinal axis.

17. The end effector of claim 1, wherein a cross-section of the first jaw member at a location including the first raised step includes the first tissue contact surface consisting of the two horizontal walls interconnected by the single vertical wall of the first raised step.

18. The end effector of claim 17, wherein the tissue contact surface of the second jaw member includes a single vertical wall that is parallel to the central longitudinal axis, and wherein a cross-section of the second jaw member at a location including the second raised step includes the second tissue contact surface consisting of two horizontal walls interconnected by the single vertical wall of the second jaw member.

\* \* \* \* \*